United States Patent
Cooke

(10) Patent No.: US 8,644,909 B2
(45) Date of Patent: Feb. 4, 2014

(54) RADIOGRAPHIC IMAGING METHOD AND APPARATUS

(76) Inventor: T. Derek V. Cooke, Maberly (CA)

(*) Notice: Subject to any disclaimer, the term of this patent is extended or adjusted under 35 U.S.C. 154(b) by 359 days.

(21) Appl. No.: 13/016,485

(22) Filed: Jan. 28, 2011

(65) Prior Publication Data

US 2011/0191084 A1 Aug. 4, 2011

Related U.S. Application Data

(63) Continuation-in-part of application No. 11/827,600, filed on Jul. 12, 2007, now abandoned.

(51) Int. Cl.
A61B 5/00 (2006.01)
(52) U.S. Cl.
USPC ............ 600/429; 600/407; 600/425; 600/426
(58) Field of Classification Search
USPC ..................... 600/407, 424, 425, 426, 429
See application file for complete search history.

(56) References Cited

U.S. PATENT DOCUMENTS

| | | | |
|---|---|---|---|
| 4,841,967 A * | 6/1989 | Chang et al. | 606/130 |
| 5,464,410 A * | 11/1995 | Skeens et al. | 606/130 |
| 5,923,727 A | 7/1999 | Navab | |
| 5,951,475 A | 9/1999 | Gueziec et al. | |
| 5,967,982 A | 10/1999 | Barnett | |
| 6,050,724 A | 4/2000 | Schmitz et al. | |
| 6,379,041 B1 | 4/2002 | Schuetz et al. | |
| 6,978,166 B2 | 12/2005 | Foley et al. | |
| 2003/0088179 A1 | 5/2003 | Seeley et al. | |
| 2003/0139663 A1 | 7/2003 | Graumann | |
| 2004/0068187 A1 | 4/2004 | Krause et al. | |
| 2004/0199072 A1 | 10/2004 | Sprouse et al. | |
| 2006/0155189 A1 | 7/2006 | Lavallee et al. | |
| 2006/0204067 A1 | 9/2006 | Tuma et al. | |

* cited by examiner

Primary Examiner — Peter Luong
(74) Attorney, Agent, or Firm — Greer, Burns & Crain, Ltd.

(57) ABSTRACT

A reference frame is described for use in a radiographic procedure. The reference frame is positionable relative to a joint or bone to be imaged, and is radio-transparent. The frame has embedded or affixed thereto a plurality of computer recognizable radio opaque markers. A method of obtaining three dimensional images of bones and joints using the frame is described.

6 Claims, 4 Drawing Sheets

RADIOGRAPHIC IMAGING METHOD AND APPARATUS

PRIORITY CLAIM

This application is a continuation-in-part application of U.S. patent application Ser. No. 11/827,600 filed on Jul. 12, 2007 now abandoned.

BACKGROUND

The present invention relates to the field of radiographic imaging. In particular, the present invention provides a method and apparatus for generating accurate 3D models from 2D calibrated images. The method and apparatus of the present invention are useful in planning surgery and in sizing of orthopaedic implants, particularly when the joint or bone being supplemented or replaced has been damaged by injury or disease. The present invention may also be used in custom implant manufacture and fit.

In orthopaedic surgery the replacement of bone and joint parts is now in common use for disorders due to arthritis, prior injury, disease. Generally, at surgery, the part to be replaced is matched to the available parts in a given tool set using variously sized cutting blocks and trial implants. In many instances the trial parts do not fit the specific part accurately and the surgeon must decide to use a smaller or larger size.

As a means to solve this poor fit problem, CT and MRI imaging techniques have been used to generate specific, customized 3D models of the specific part to be replaced. From these models, using CAD/CAM techniques, a custom implant can be created. Cutting tools and blocks are needed to perfect the fit. But the use of CT and MRI imaging techniques are expensive, time consuming and not widely available.

One example of a specialized imaging system, that can generate an electronic model of a bone or joint is described by Sprouse et al. in US 2004/0199072, which describes a device that uses a coil array to generate a low energy magnetic filed around a patient. Sensors measure field strength at point in the field that are touched by a probe to build a 3D image of a bone or joint. The probe only touches the skin over-lying the bone or joint, so variations in soft-tissue depths, from patient to patient render this method somewhat inaccurate. Moreover, the physician using this method will not be provided with an actual image of the bone or joint in question, so anomalies in same cannot be assessed.

Bones and joints are irregular, biological vitally important structural elements of the mammalian skeleton.

The skeleton provides the structural support of vital organs (heart, liver, lungs) and the rigid entities (long bones) linked to mobile entities (joints) on which muscles, tendons and ligaments are set to provide motion.

Disease affects the musculoskeletal system in forms of joint disease, (arthritis) and bone deformity (fractures, infections, growth disorders). For correction of these maladies the medical and veterinarian community use images made using radiographs (most commonly radiographs such as X-Rays). The views made are uni-planar images which profile the skeletal structures relative to the muscular ones based on the high mineral content in the skeleton (osseous components of the bones and joints).

The difficulty in the interpretation of the images of the diseased M/S entities is the inherent variation and irregularities of the structures based on individual differences, which in turn are modified by disease. Thus in the human knee joint there are subtle differences in size (males larger than females) and shape (Asian versus western) yet shared general geometric and functional characteristics. Disease such as arthritis damages the joint's surfaces and modifies the shape and its structural/functional integrity. Examples are the common bow legged deformity and medial (inner) joint space collapse seen in Osteoarthritis affecting the medial compartment of the knee.

SUMMARY

Accuracy and reproducibility of the images of these structures are importantly affected by position (especially rotation and flexion) and by parallax and distortion (due to the point source of the radiographic beam and the variations in distances applied in uncontrolled ways for the source, region of interest and the imaging receptor. The corrections of these problems is dealt with in the present invention by use of modules that ensure reliable positioning of the part and calibration radio dense markers in known relation to each other in the module structure which when imaged may be used to correct the errors due to parallax and distortion.

Computational image analysis according to the present invention is optimally undertaken using the positional set ups and distortion correction means as described above. The application uses readily recognizable bone and joint anatomic features (bone landmarks) common to all similar structures in mammals.

These landmarks are selected as constant features of long bones and the articular entities of their linking joints. For example, in the lower extremity, the limb's frontal alignment may be defined as neutral, varus (bow legged) or valgus (knock kneed) by the mechanical axes (MAs) of the thigh bone (femur) and the shin bone (tibia).

These in turn may be measured by the angles formed by the linear extension of the lines (of these respective axes) as they cross the knee in the frontal plane (neutral co linear, varus angled outwards, valgus angle apex inwards). For example the femur MA is the line extending from the femoral head centre at the hip joint proximally and the apex of the intercondylar notch of the femur distally. Similarly, the tibial MA is defined as the mid interspinous points of the tibial plateau proximally extending to the mid tibial plafond distally at the ankle. Thus the definition of the four points or reproducible bone landmarks in the 2 bones provides the axes of the limb and the angular orientation the alignment of the limb. Frontal alignment may then be further described as the Hip-Knee-Ankle angle (HKA).

The present invention uses the four points gathered from a digital image of the limb's X-ray and provides algorithms that automatically calculate the HKA. In addition to the HKA, the use of tangents at the knee's articular surfaces may be defined by bone landmarks at the femoral and tibial medial and lateral margins respectively to provide measurements of the bone and joint contributions to the HKA. The angles so defined may include the condylar hip angle (CH measures the femoral contribution to HKA), the condylar plateau angle (CP the joint surface contribution) and the plateau ankle angle (PA the contribution of the tibia). These angles are related by the equation:

$$HKA=CH+CP+PA \tag{1}$$

The clinical use of the data derived from the computational derivation of HKA and its components is the understanding of the given limb alignment and, in the case of deformity, the location and extent of the parts (bone or joint or combined) producing it. From this information specific plans may be made for correction by bone realignment or joint reconstruction.

The means to gather the coordinate data of the bone landmarks is provided by a number of options. The first is the use of electronic tools in the form of circles, straight lines, rulers, parallel lines and points, which under the users guidance are applied to the selected digital image to define the point (landmark).

Thus, as an example, the femoral head centre (FHC) is readily defined as the centre of an electronic circle tool activated over the femoral head then dragged at its margins to fit the head's outline. A software algorithm records the x-y coordinates of this point as it marks the FHC the proximal point of the Femoral MA and HKA angle. An electronic ruler and a point tool may be used to define the distal femoral point in the apex of the intercondylar notch (FIC point) as shown on the same image. When activated the software then defines this FIC landmark's x-y coordinates relative to FHC and displays the MA and define its length in pixels.

If the image is calibrated, the pixel length is automatically converted to the femoral bone length in mm. When a set of landmarks is defined in this way a series of specific solutions that describe the bone and joint geometry and dimensions may be readily produced. These constitute the computational analysis of the limb parts being imaged. This also includes the use of pattern recognition and edge detection techniques which, when appropriately applied to the specific bone will automatically define the FHC and FIC landmarks.

The present invention provides a computer based methodology that accurately determines the spatial geometry of bone and joint parts from radiographic images, having also the capacity to derive 3D shapes of the part from two or more radiographic images taken in known orientations.

A. The method incorporates:

1. Positional aids to provide for reliable and repeatable images.
2. The selective use of bone and joint landmarks.
3. Calibration modules to allow the correction of parallax and image distortion.
4. Software, compatible with industry standards (currently DICOM3, HLA 7), embodying a series of electronic tools used for the identification and localization of calibration markers and bone and joint landmarks.
5. Software algorithms that compute these acquired data to provide the special and dimensional specifics desired
6. Software that incorporates image definition, edge detection and other suitable applications as a means to automate the image recognition for the derivation of the said geometry and shapes.

Further, the present invention provides a system for analysis of radiographic and other related imaging modalities (ultrasound, visual, magnetic resonance, tomography etc) of mammalian parts in digital form.

This system is designed to be used with analogue radiographic imaging systems, (images transferred to digital form by photographic or scanning means) or preferably with digital forms of Computer Radiography or Direct Radiography.

This aspect of the present invention comprises a means to a. reliably and reproducibly produce radiographic and other related image(s) in digital form obtained in one, two or more planes of known orientation, one to itself and to the others (as an example two images at right angles to each other), b. a means to acquire the radiographic image from DICOM or other forms of electronic files, c. a means to optimize the visualization of obtained image, d. a means comprising specialized tools by which measurements are made on objects, which objects may include registration markers provided to be visible in the imaged field, as an object of interest (such as a knee joint), e. a means for gathering said measurements as X-Y coordinates to each other, f. a means for transfer of the selected identifiable features of said registration (calibration) markers and objects measured features in recordable form as data, g. a means for storing and reproducing said measurement data for review, h. a means to correct errors of parallax and distortion of said data by the use of the information derived from the pre-mentioned calibration markers, the means thereby to provide levels of known precision for measurements of said radiographic image to tolerances far beyond those obtained by positional means alone, and including; i. means to modify the scalar measurements suitably to meet tolerance standards to appropriately fit implants in bones and joint parts, j. a means to use the coordinate data gathered from one segment of the image to derive geometric properties of the part being imaged, and its relationship to other parts within the imaged field, k. the means to link coordinate data obtained from one spatially separate image to another, l. the means to derive mathematical solutions from the analysis of said coordinate data when derived from different parts of the image (for instance the position, geometry and the alignment of knee parts with respect to the hip joint of a given subject from two separated segments of the same image or two images [one of the hip, one of the knee] linked by means of coordinate registration markers), m. a means to create 3 dimensional (3D) models in electronic form from spatially oriented images obtained in defined coordinates one to the other.

This method of the present invention is designed to be applied/used with analogue radiographic imaging systems or preferably with digital forms of Computer Radiography or Direct Radiography.

In the method of the present invention modules in the form of guides or frames located at strategically selected positions with relation to the mammalian part (for instance at levels of interest in or around the human knee) are used to reliably and repeatably position the limb part in a given orientation (eg a frontal or a lateral position). The modules provide the location for cassette holders or for like electronic receiving receptors, set in desirable locations so as to obtain reliable and repeatable images in selected specific orientations (such as obtaining frontal, lateral, oblique images at known orientations one to the other) of the part. A registration system consisting of radio opaque markers at predefined locations, said markers being in differing forms, distinguishable from one to another, set in geometric coordinates (such as a right angles) to each other in the exterior parts of the said modules. Patterns of markers that can be more easily recognized by software may also be utilized. Electronic programs are utilized, by which radiographic images (such as DICOM or other related file forms) of the selected parts obtained in the ways outlined above are visualized. Programs also may improve the visualization of the image. Program software provides a wide selection of measurement tools in electronic form (line, ruler, angles, circle, midline with various functional characteristics for adding right angles or parallel lines). Software tools are used to measure objects in the image, including registration marker locations and the geometric information of desired imaged parts (knee joint angles or linear dimensions) and store said coordinates in mathematical form to derive linear and geometric information about said calibration markers and imaged object. Mathematical solutions are applied to these collected data to correct the errors induced by parallax and distortion and mathematical algorithms applied to the coordinate corrected data obtained form image used to derive select information such as the frontal leg alignment angles and leg lengths.

In the method of the present invention, then, a data set defining a three dimensional image consisting of selected landmarks and radiographic markers is related, which can then be composed to other data sets in a database, to determine a close match (it being understood that no two bones or joints are identical) that can be used to model a three dimensional image of the bone or joint, in undamaged condition for the use of a surgeon in selecting an implant, planning surgery, or making a custom implant.

In a broad aspect, then, the present invention relates to a method of imaging a bone or joint comprising the steps of:

a) positioning a bone or joint in a frame relative to an x-ray imaging apparatus having a source of radiation at a first location and keeping said bone or joint still throughout the entire method;

b) said frame having a first plate containing radio-opaque markers at known locations between the source of radiation and a first image capture surface, whereby at least two said radio-opaque markers in said first plate are located a plane at a known angle relative to said first image capture surface and between the bone or joint part and the sources of radiation;

c) said frame having a second plate containing radio-opaque markers at known locations between the source of radiation and said first image capture surface, whereby at least two said radio-opaque markers in said second plate are located a plane at a known angle relative to said first image capture surface and between the bone or joint part and the first image capture surface;

d) irradiating said bone or joint to be imaged, and said first image capture surface to obtain a first x-ray image including images of the markers in said first and said second plate, and then removing said first image capture surface;

e) moving said source of radiation to a second location;

f) positioning a second image capture surface proximate to said bone or joint;

g) said frame having a third plate containing radio-opaque markers at known locations between said second source of radiation and said second image capture surface whereby at least two said radio-opaque markers in said third plate are located in a plane at a known angle to said second image capture surface and between the bone or joint part and the second source of radiation;

h) said frame having a fourth plate containing radio-opaque markers at known locations between the second source of radiation and said second image capture surface, whereby at least two said radio-opaque markers in said fourth plate are located a plane at a known angle relative to said second image capture surface and between the bone or joint part and the second image capture surface i) irradiating said bone or joint to be imaged and said second image capture surface to obtain a second x-ray image including images of markers in said second plate j) establishing the position of said source of radiation relative to said first x-ray image by calculating the point of intersection in space of a pair of lines, each line being from the image of a pair of radio opaque marker on said first x-ray image, through the actual known location of that radio opaque marker, to the source of radiation;

k) establishing the position of said source of radiation relative to said second x-ray image by calculating the point of intersection in space of a pair of lines, each line being from the image of a pair of radio opaque marker on said second image, through the actual location of said radio opaque marker, to the source of radiation;

l) locating a plurality of anatomical landmark sites on said first and second x-ray images and calculating, for each landmark site the path of a line from said source of radiation through the landmark site to the respective image capture surface, and then calculating, for each said landmark site, the point of intersection in three-dimensional space, of the lines from the source of radiation to the respective image capture surface, thereby to obtain the location in three-dimensional space of each of a plurality of landmark sites of said bone;

m) comparing the locations of said landmark sites to the locations of similar landmark sites on a three-dimensional digital model of a bone or joint having known dimensions; and n) adjusting said three-dimensional model by changing the landmark locations to those calculated in respect of the imaged bone to obtain a three-dimensional model of the imaged bone or joint.

Preferably, the radio opaque markers are embedded in a radio-transparent reference frame dimensioned to be placed in proximity to a bone or joint.

Moreover, said reference frame preferably comprises patterns of radio opaque markers embedded therein.

Each marker in a plate may be a different shape than the rest of the markers in said plate.

All markers in said frame may be of different shapes.

The fourth plate may be removable from said frame, for placement on said frame after a bone or joint is placed in said frame.

The term 'landmark', as used herein, refers to anatomic features such as crests, ridges, tendon or ligament attachment sites and the like, that can be reliably and repeatedly located with precision on a bone, and show little or no variation in location on the bone from subject to subject. Moreover, the term 'landmark' may be taken as including distinct profiles and shapes, especially those that, in known orientation can be recognized by appropriate software.

In another broad aspect the present invention relates to a reference frame for use in a radiographic procedure, said reference frame being positionable relative to a joint or bone to be imaged, and being radio-transparent, and having embedded or affixed thereto a plurality of computer recognizable radio opaque markers.

BRIEF DESCRIPTION OF THE DRAWINGS

In order to carry out the present invention, as noted specific guides, or frames will preferably be used, and are illustrated, by example, with reference to the following drawings, in which.

DETAILED DESCRIPTION

Figure 1:
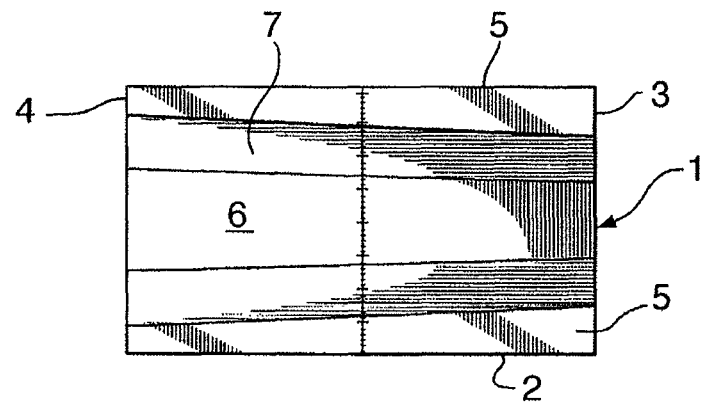
FIG. 1 is a top view of a leg holding frame for holding a leg while the knee is imaged.
Figure 2:
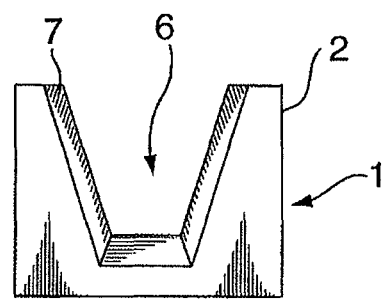
FIG. 2 is a front view of the frame of FIG. 1.

Referring now to FIGS. 1-4, a suitable frame for immobilizing a leg during x-ray imaging is shown. The frame conspires a leg holder 1 having vertical side walls 2. End walls 3.4 may be provided, to ensure rigidity of the entire structure. Top walls 5 extend the length of the leg holder, from end to end, and flank a channel 6 that extends the length of the leg holder.

Figure 3:
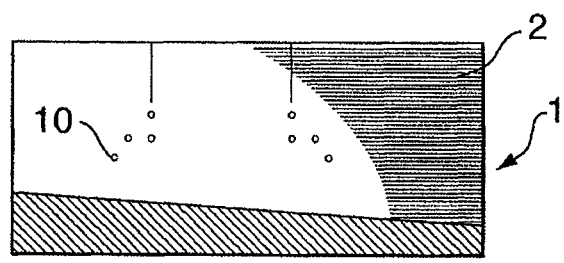
FIG. 3 is a side view of the frame of FIG. 1.

The function of the channel 6 is to accommodate a leg therein, so as shown in FIG. 3, the channel will incline and converge slightly towards the foot end thereof.

Channel 6 has inclined walls 7 and a floor 8 that are preferably lined with a thin foam liner 9 that will make the leg more comfortable in the holder and also permit the leg to settle so as not to move between imaging steps, as will be explained below.

The entire leg holder, including the foam lining 9 is fabricated from a radio-transparent material such as lucite or any other suitable material.

A plurality of radio-opaque markers 10 are embedded in the two side walls 2 of the leg holder, opposite the middle area thereof, so that they will appear on an x-ray image of a knee. The markers may be simple lead beads, but preferably, each marker is a unique computer identifiable shape and/or part of a computer recognizable pattern, for reasons that will be explained below.

Figure 4:
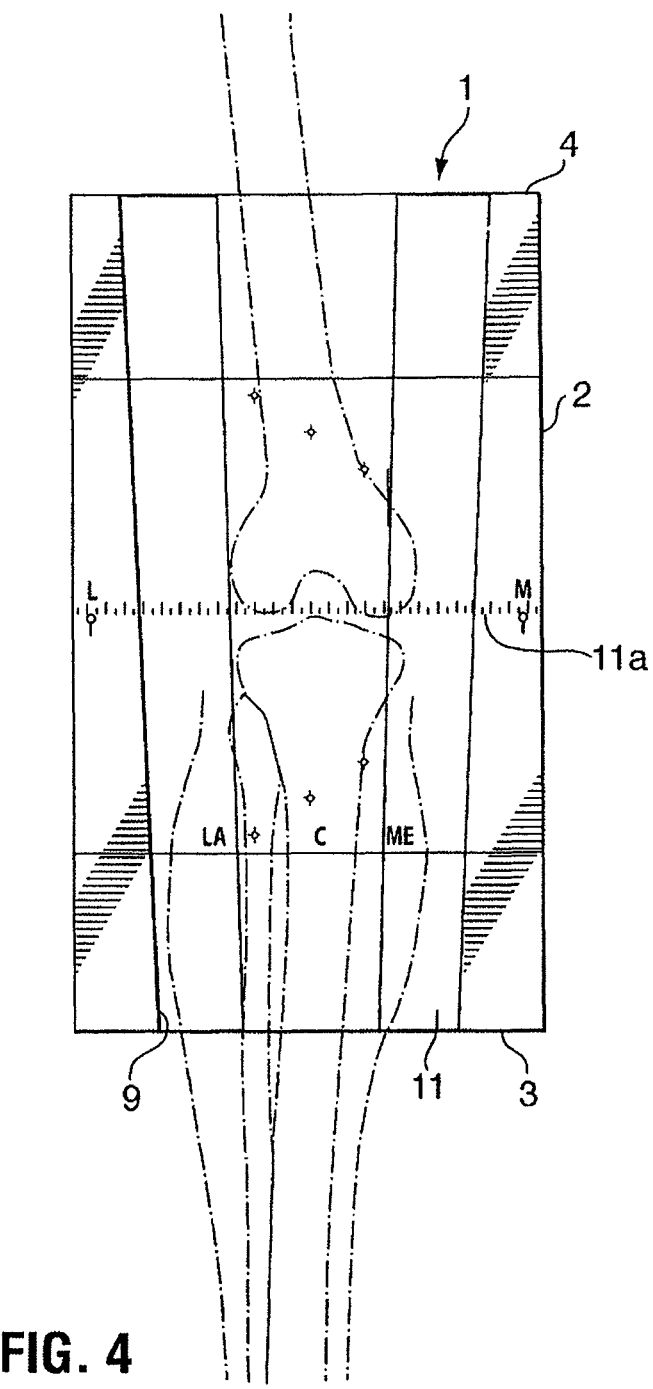
FIG. 4 is a side view of the frame of FIG. 1, showing a leg, including a knee joint, in the leg holding frame.
Figure 5:
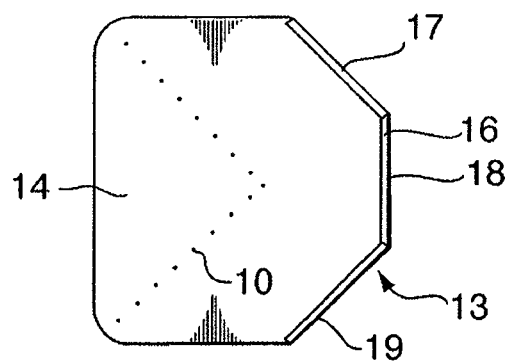
FIG. 5 is a top view of a hip reference frame for use in the present invention.
Figure 6:
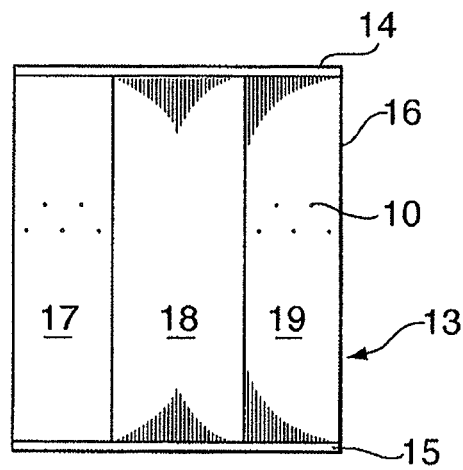
FIG. 6 is a front view of the reference frame of FIG. 5.
Figure 7:
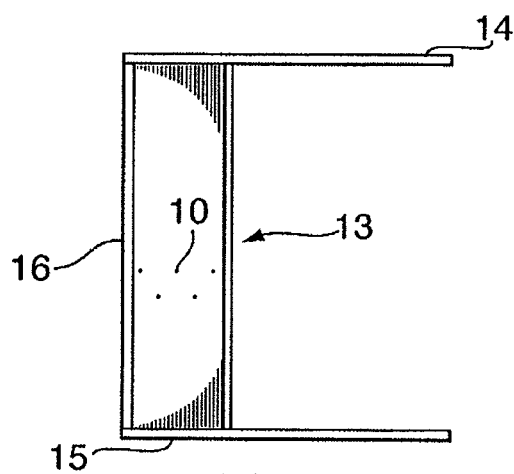
FIG. 7 is a side view of the reference frame of FIG. 5.
Figure 8:
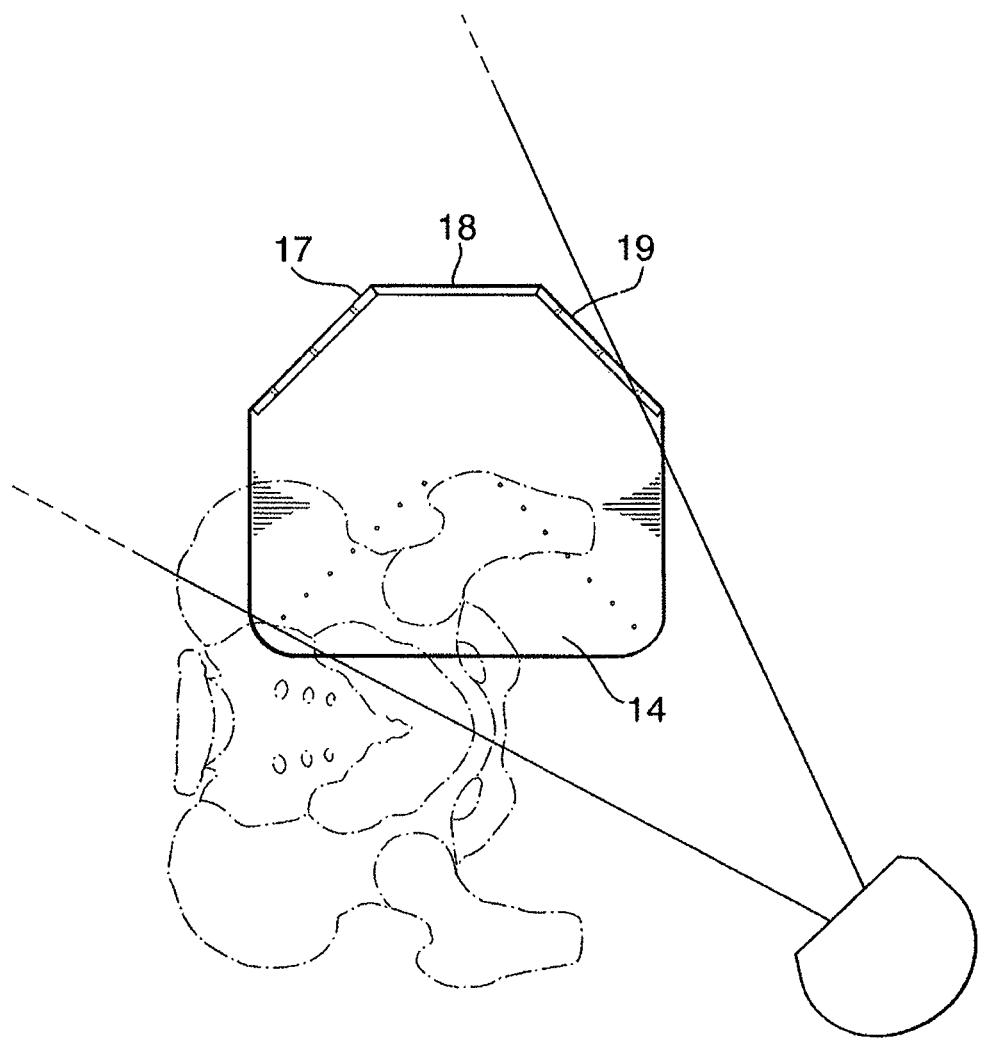
FIG. 8 is a top view of the reference frame, in position relative to the pelvic region of a patient.

Lastly, as can be seen most clearly in FIG. 4, a transparent plate 11 (i.e., preferably both radio and visible light transparent) provided with a measuring scale or ruler 11a made of radio opaque material is provided, to be placed on top of the top walls 5 when the leg has been placed in the holder.

In terms of the method described above, the two inclined walls 7 are considered the first and second plates. The floor 8 of channel 6 is the third plate, and the transparent plate 11 that is placed on top of the leg holder is the fourth plate.

Since the manner of use of the leg holder and the pelvic or hips reference frame shown in FIGS. 5-8 is very similar, a description of the hip reference frame follows:

Referring to FIGS. 5-8, a hip reference frame 13 is provided. Frame 13 consists of a top plate 14, a bottom plate 15, and an upright plate 16. As illustrated, the upright plate 16 may comprise three panels 17, 18 and 19, with the side panels 17, 19 being angled with respect to the central panel 18. The purpose of angling the panels is to provide structural rigidity to the frame, and to provide a surface, i.e. one of the side panels 17, that can be oriented parallel to an image sizing surface, and another surface, 19 that is substantially normal thereto. While such an arrangement may be considered ideal, it is not essential, because the selection of materials can compensate for the relative position of panels to provide rigidity, and other function of the upright plate, as will be discussed below, to carry fixed, radio opaque markers, required only that the markers be recognizable either by a computer or a technician, and that they remain in a fixed position.

The upper panel, lower panel and upright panel are each made from a radio-transparent material and will preferably also be made from a visible light transparent material, for ease of positioning. As noted above, a plurality of radio opaque markers 10 are affixed to or embedded in the plates 14, 15 and 16. The markers are distinctive, computer recognizable shapes and/or will be in computer recognizable patterns.

As regards the method of the present invention, plates 15 and 14 may be considered the first and second plates, while plates 17 and 19 are the third and fourth plates.

The function of the frames, and markers provided in the present invention is to provide a three dimensional network of markers in known locations so that when an x-ray image of a bone or joint is taken with the bone or joint in the reference frame, the image of the known network of markers is also captured. If a second image is then taken of the same bone or joint, without having moved the bone (or joint) or the reference frame, the three dimensional location of identifiable landmarks on the bone can then be determined, according to the method of the present invention, which may be implemented by computer. Preferably, the second image is taken at 90° to the first. The selection of 90° is because it will render a pair of x-ray images that can be more easily received and correlated by a person seeing them. As to determination of landmark location by computer, it is desirable that the second image be taken at a known angle relative to the first.

Once the location in space of at least two, but preferably more, landmarks is known, software will compare those locations with ideal locations derived from a large database of three dimensional image models, and will select a close match as a three dimensional model of the bone being imaged. Accordingly, the method of the present invention, using the reference frames of the present invention, is able to generate a fairly complete three dimensional image of a bone or joint after having taken only two x-rays—many fewer than the number required to generate a three dimensional image using conventional CT scanning. Moreover, the method of the present invention does not require use of an unconventional imaging system, such as that taught in US 2004/0199072 A1 by Sprouse et al.

While it is true that the three dimensional image produced by the present invention will not show the particular damage or abnormalities associated with a bone or a joint, it will provide very useful information that can be used to select an implant size, or plan surgery.

In the method of the present invention, the location of landmarks is currently a task that must be undertaken by an individual. That is, the individual selects several landmarks that are visible on each of the two images, and enters the co-ordinates (manually, by a touch screen or with a mouse click) of each landmark on each x-ray image. Since the landmark will not have changed actual position in space or position in space relative to the markers that the computer can locate and identify in each image, and the relative angle at which each image was taken will be known, then calculation of the position in space of each landmark, and assigning a three dimensional coordinate to it will not be difficult. Matching the co-ordinates of a pair of landmarks to the co-ordinates of those same landmarks in a database of healthy bones and joints will be a fairly simple task.

It will be understood, however, that landmarks, or bone shapes and profiles, may also be recognized by appropriate computer software, and similar results obtained.

In summary, then, the present invention, by the use of simple but novel reference frames, examples of which have been shown for the knee and the hip/pelvis, provides a means by which a three dimensional model of a joint or bone can be made with only two e-ray images being required.

While several particular embodiments of the present method have been shown and described, it will be appreciated by those skilled in the art that changes and modifications may be made thereto without departing from the invention in its broader aspects and as set forth in the following claims.

The invention claimed is:

1. A method of imaging a bone or joint comprising the steps of:
   a) positioning a bone or joint in a frame relative to an x-ray imaging apparatus having a source of radiation at a first location and keeping said bone or joint still throughout the entire method;
   b) said frame having a first plate containing radio-opaque markers at known locations between the source of radiation and a first image capture surface, whereby at least two said radio-opaque markers in said first plate are located a plane at a known angle relative to said first image capture surface and between the bone or joint part and the sources of radiation;

c) said frame having a second plate containing radio-opaque markers at known locations between the source of radiation and said first image capture surface, whereby at least two said radio-opaque markers in said second plate are located a plane at a known angle relative to said first image capture surface and between the bone or joint part and the first image capture surface;

d) irradiating said bone or joint to be imaged, and said first image capture surface to obtain a first x-ray image including images of the markers in said first and said second plate, and then removing said first image capture surface;

e) moving said source of radiation to a second location;

f) positioning a second image capture surface proximate to said bone or joint;

g) said frame having a third plate containing radio-opaque markers at known locations between said second source of radiation and said second image capture surface whereby at least two said radio-opaque markers in said third plate are located in a plane at a known angle to said second image capture surface and between the bone or joint part and the second source of radiation;

h) said frame having a fourth plate containing radio-opaque markers at known locations between the second source of radiation and said second image capture surface, whereby at least two said radio-opaque markers in said fourth plate are located a plane at a known angle relative to said second image capture surface and between the bone or joint part and the second image capture surface i) irradiating said bone or joint to be imaged and said second image capture surface to obtain a second x-ray image including images of markers in said second plate j) establishing the position of said source of radiation relative to said first x-ray image by calculating the point of intersection in space of a pair of lines, each line being from the image of a pair of radio opaque marker on said first x-ray image, through the actual known location of that radio opaque marker, to the source of radiation;

k) establishing the position of said source of radiation relative to said second x-ray image by calculating the point of intersection in space of a pair of lines, each line being from the image of a pair of radio opaque marker on said second image, through the actual location of said radio opaque marker, to the source of radiation;

l) locating a plurality of anatomical landmark sites on said first and second x-ray images and calculating, for each landmark site the path of a line from said source of radiation through the landmark site to the respective image capture surface, and then calculating, for each said landmark site, the point of intersection in three-dimensional space, of the lines from the source of radiation to the respective image capture surface, thereby to obtain the location in three-dimensional space of each of a plurality of landmark sites of said bone;

m) comparing the locations of said landmark sites to the locations of similar landmark sites on a three-dimensional digital model of a bone or joint having known dimensions; and n) adjusting said three-dimensional model by changing the landmark locations to those calculated in respect of the imaged bone to obtain a three-dimensional model of the imaged bone or joint.

2. The method as claimed in claim 1, wherein said radio opaque markers are embedded in a radio-transparent reference frame dimensioned to be placed in proximity to a bone or joint.

3. The method as claimed in claim 2, wherein said reference frame comprises patterns of radio opaque markers embedded therein.

4. The method as claimed in claim 3, wherein each marker in a plate is a different shape than the rest of the markers in said plate.

5. The method as claimed in claim 4, wherein all markers in said frame are different shapes.

6. The method as claimed in claim 1, wherein said fourth plate is removable from said frame, for placement on said frame after a bone or joint is placed in said frame.

\* \* \* \* \*